United States Patent
Hsu et al.

(10) Patent No.: US 6,468,214 B2
(45) Date of Patent: Oct. 22, 2002

(54) APPARATUS FOR HUMAN INTERFACES OF AN ULTRASONIC DIAGNOSTIC SYSTEM

(75) Inventors: E-Chang Hsu, Hsinchu (TW); Hung-Chi Huang, Hsinchu (TW); Jiann-Hwa Jeng, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 09/734,365

(22) Filed: Dec. 11, 2000

(65) Prior Publication Data

US 2002/0052548 A1 May 2, 2002

(51) Int. Cl.$^7$ .................................................. A61B 8/00
(52) U.S. Cl. ........................................................ 600/437
(58) Field of Search ............................ 600/437, 443, 600/447

(56) References Cited

U.S. PATENT DOCUMENTS

| | | |
|---|---|---|
| 5,590,658 A | 1/1997 | Chiang et al. |
| 5,795,297 A | 8/1998 | Daigle |
| 6,015,385 A | 1/2000 | Finger et al. |
| 6,171,244 B1 * | 1/2001 | Finger et al. ............... 600/437 |

FOREIGN PATENT DOCUMENTS

WO       WO09515521 A2      6/1995

* cited by examiner

Primary Examiner—Francis J. Jaworski
(74) Attorney, Agent, or Firm—Senniger, Powers, Leavitt & Roedel

(57) ABSTRACT

The present invention discloses an apparatus for human interfaces of an ultrasonic diagnostic system based on a personal computer. The apparatus can be applied in the input end and output end of the system. Only the normal keyboard of a personal computer is needed for the present invention, instead of further designing a customized control interface used in prior art. Besides, a digital display controller is used to control output signals of a scanner, which are stored in a video memory. The output frequency of the digital display controller is the same with that of the personal computer. Therefore, a lot of unnecessary transformations between different video signal formats seen usually in prior art can be avoided. Besides, system complexity and manufacturing cost will be reduced, and the power consumption will be also saved.

6 Claims, 4 Drawing Sheets

APPARATUS FOR HUMAN INTERFACES OF AN ULTRASONIC DIAGNOSTIC SYSTEM

BACKGROUND OF THE INVENTION

1. Field of the Invention

The present invention relates to an apparatus for human interfaces of an ultrasonic diagnostic system, and particularly to an apparatus for human interfaces of an ultrasonic diagnostic system based on a personal computer.

2. Description of the Related Art

The apparatus for human interfaces of an ultrasonic diagnostic system generally comprises: an input device such as a keyboard, tracking ball and mouse, a hard disk, and a monitor. Most ultrasonic diagnostic systems in the market have a customized circuit for controlling human interfaces, and storage formats of the ultrasonic diagnostic systems are mostly not the same.

Nowadays, personal computers are very popularly used in everywhere. If data regarding medical video signals can be accepted by a personal computer, the data processing will be very convenient. To meet this requirement, a few ultrasonic diagnostic systems in the market utilize a personal computer to control the data processing, and use a keyboard as a human interface. However, some special keys used by a doctor are not shown in a normal keyboard of a personal computer, and a customized panel portion and control interface are needed to be further provided to communicate with the personal computer. The above description is disclosed in U.S. Pat. No. 5,795,297. Besides, in displaying images, video capturing cards are needed to capture ultrasonic video signals from the output of the ultrasonic diagnostic system, and the ultrasonic video signals are then delivered to the monitor of the personal computer. The above description is disclosed in U.S. Pat. Nos. 6,015,385, 5,795,297 and 5,590,658 and also disclosed in WO 95/15521.

Unfortunately, video signals inside the ultrasonic diagnostic system are transmitted in a digital format, and before the video signals reach the output end, a digital-to-analog converter is needed to process for meeting requirements by a video capturing card, and an analog-to-digital converting is needed to process for meeting requirements by a personal computer. The prior art human interfaces will not only increase the power consumption of the system, but also increase design complexity and cost of the ultrasonic diagnostic system.

SUMMARY OF THE INVENTION

An object of the present invention is to provide an apparatus for human interfaces of an ultrasonic diagnostic system based on a personal computer to facilitate data processing and communication. The apparatus can be applied to an input end and output end of the ultrasonic diagnostic system.

To achieve the above object, the present invention is directed to an apparatus for human interfaces of an ultrasonic diagnostic system based on a personal computer, comprising an input data operation unit, a video display unit and a video capturing control unit. The video capturing control unit includes: a transducer connector for receiving ultrasonic feedback signals; an ultrasonic preprocessor for outputting video signals in response to the ultrasonic feedback signals; a system timing controller for controlling the output of the video from the ultrasonic preprocessor; and a host computer for receiving instructions from the input data operation unit and controlling the system operation of the ultrasonic diagnostic system and message display of the video display unit. The input data operation unit includes: a panel portion having a plurality of input device for receiving commands from a user; and a circuit portion for transferring the commands to the host computer. The video display unit includes: a digital scanning converter for converting output video signals of the ultrasonic preprocessor into digital video signals; a video display controller for controlling the output of the digital video signals; and a digital display device for selectively displaying one of the digital video signals of the video display controller and digital data signals of the host computer.

By the above structure, only the normal keyboard of a personal computer is needed for the present invention, instead of further designing a customized control interface used in prior art. Besides, a digital display controller is used to control output signals of a scanner, which are stored in a video memory. The output frequency of the digital display controller is the same with that of a personal computer; therefore a lot of unnecessary transformation between different video formats seen usually in prior art can be avoided. Besides, the system complexity and manufacturing cost will be reduced, and the power consumption will be also saved.

BRIEF DESCRIPTION OF THE DRAWINGS

The invention will be described according to the appended drawings in which.

PREFERRED EMBODIMENT OF THE PRESENT INVENTION

Figure 1:
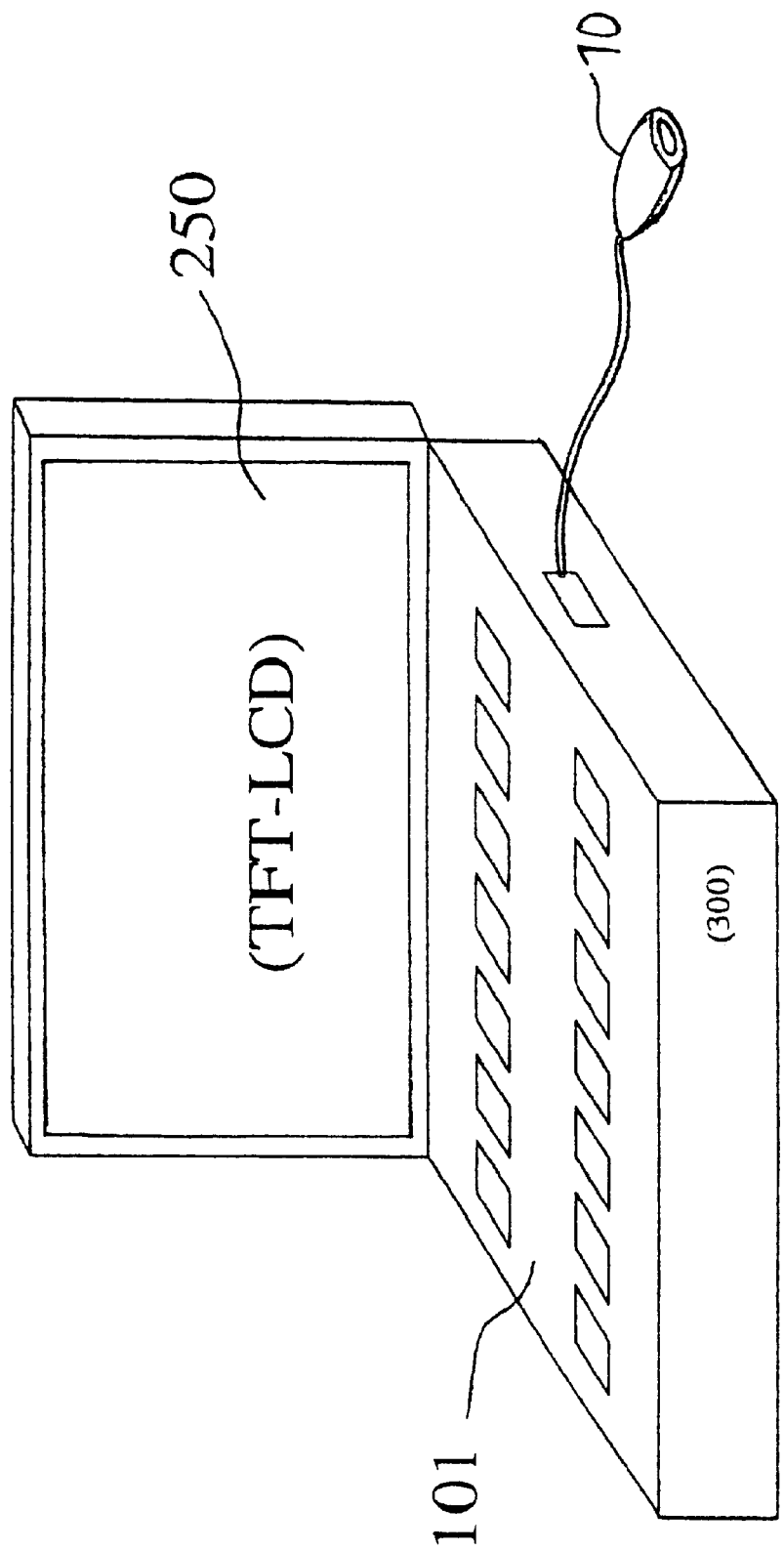
FIG. 1 shows a perspective view of an apparatus for human interfaces of an ultrasonic diagnostic system according to the present invention.

The apparatus for human interfaces of an ultrasonic diagnostic system according to the present invention comprises an input data operation unit 100, a video display unit 200 and a video capturing control unit 300. FIG. 1 shows a perspective view of the apparatus for human interfaces of an ultrasonic diagnostic system according to the present invention. In FIG. 1, a housing containing a video capturing control unit 300 therein, a panel portion 101 on a surface of the housing, a TFT-LCD 250 situated on the housing and an ultrasonic scanning head 10 connected to the video capturing control unit through a transducer are shown.

Figure 2:
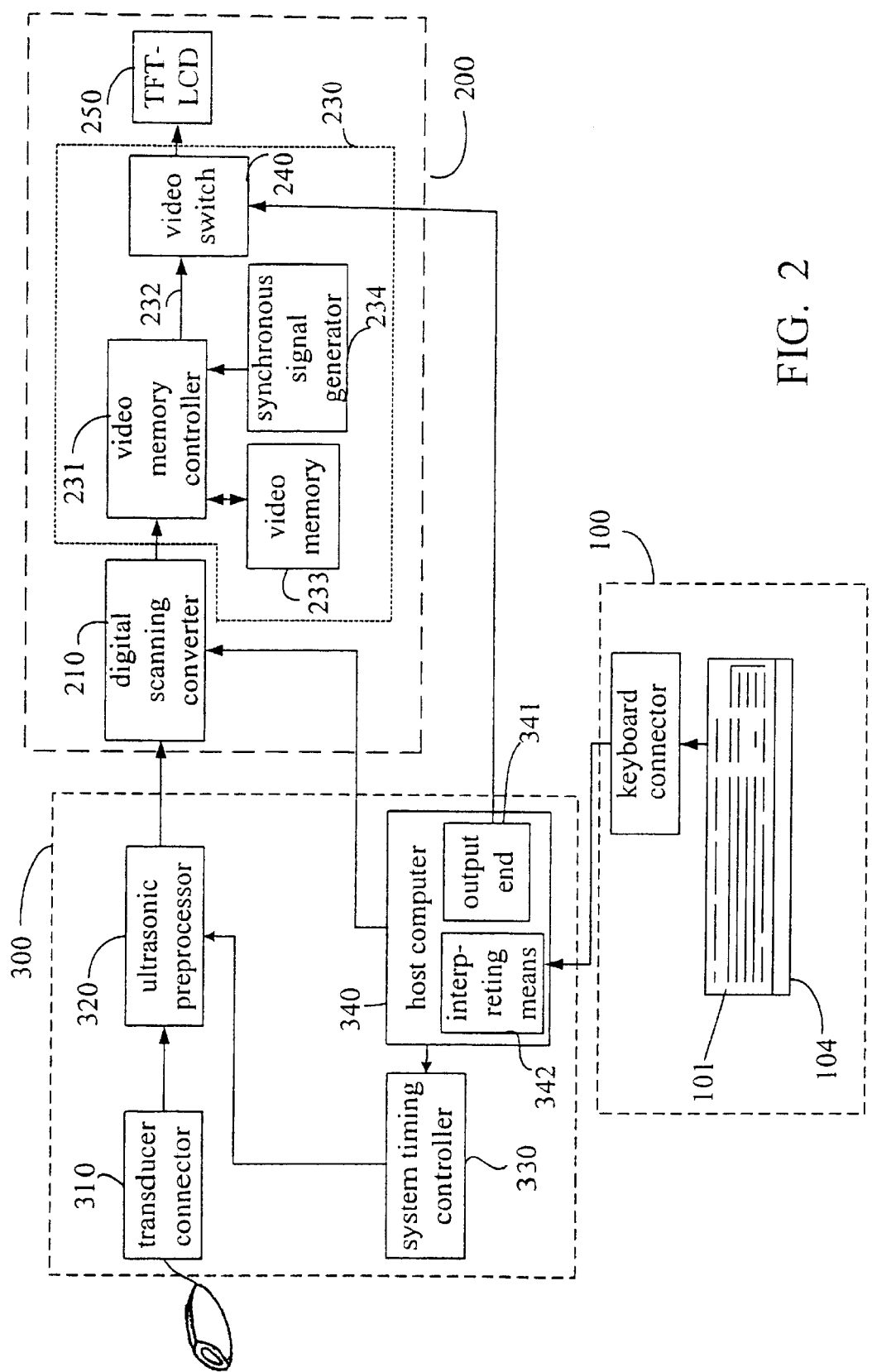
FIG. 2 shows a block diagram of the apparatus for human interfaces of an ultrasonic diagnostic system according to the present invention.

FIG. 2 shows a block diagram of the apparatus for human interfaces of an ultrasonic diagnostic system according to the present invention. In FIG. 2, the apparatus for human interfaces of an ultrasonic diagnostic system according to the present invention mainly comprises an input data operation unit 100, a video display unit 200 and a video capturing control unit 300.

Figure 3:
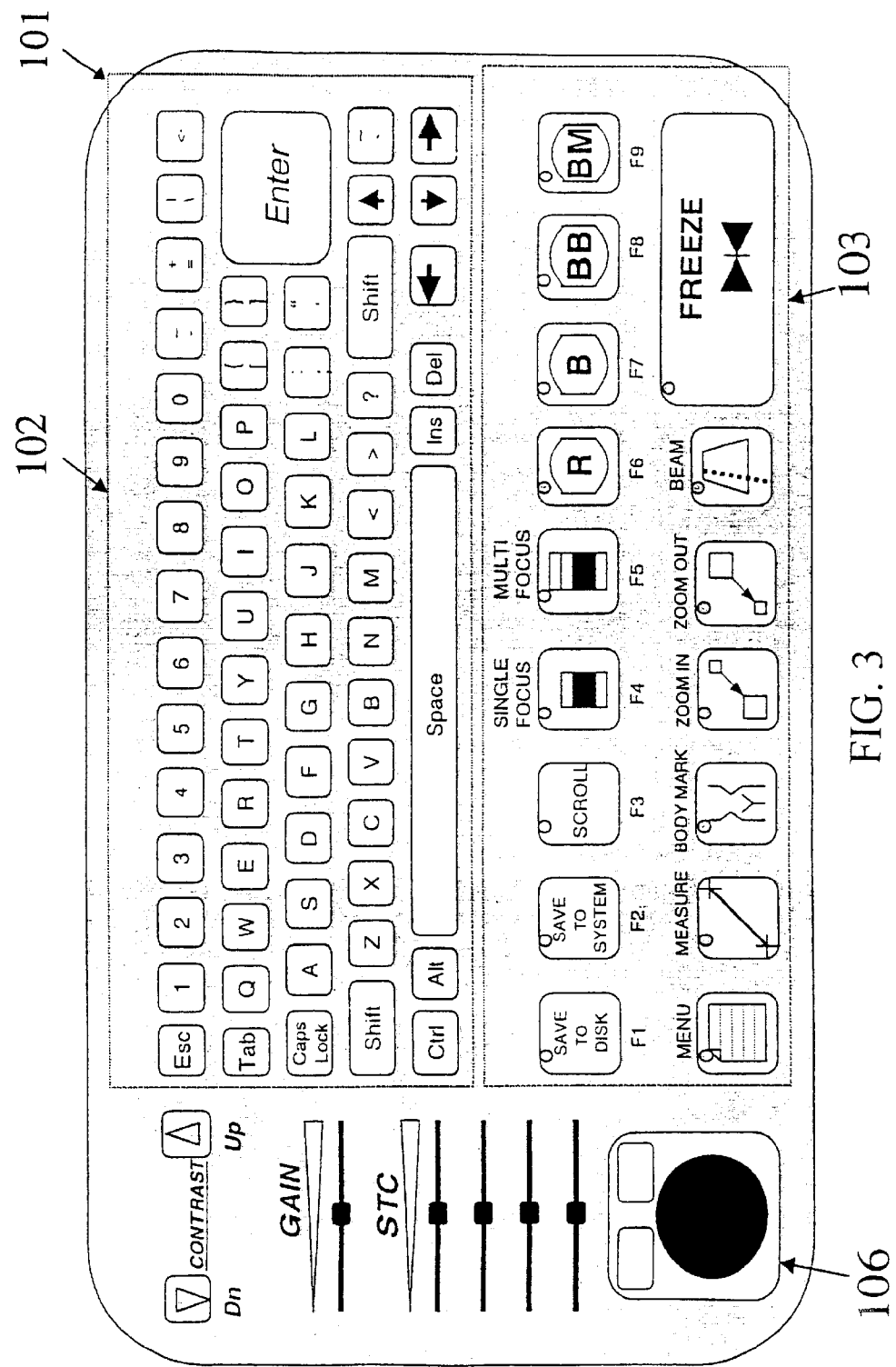
FIG. 3 shows a panel portion of the present invention.

The input data control unit 100 comprises a panel portion 101 for receiving commands from users and a circuit portion 104 for sensing the commands. The panel portion 101 will be shown in detail in FIG. 3. On the panel portion 101, there are a lot of keys such as numeric keys, alphabetical keys 102 and function keys 103, and a tracking ball 106 for inputting data and commands. The function keys are preferably located on a special position of the panel portion 101, and marked as special keys of the ultrasonic diagnostic system.

Figure 4:
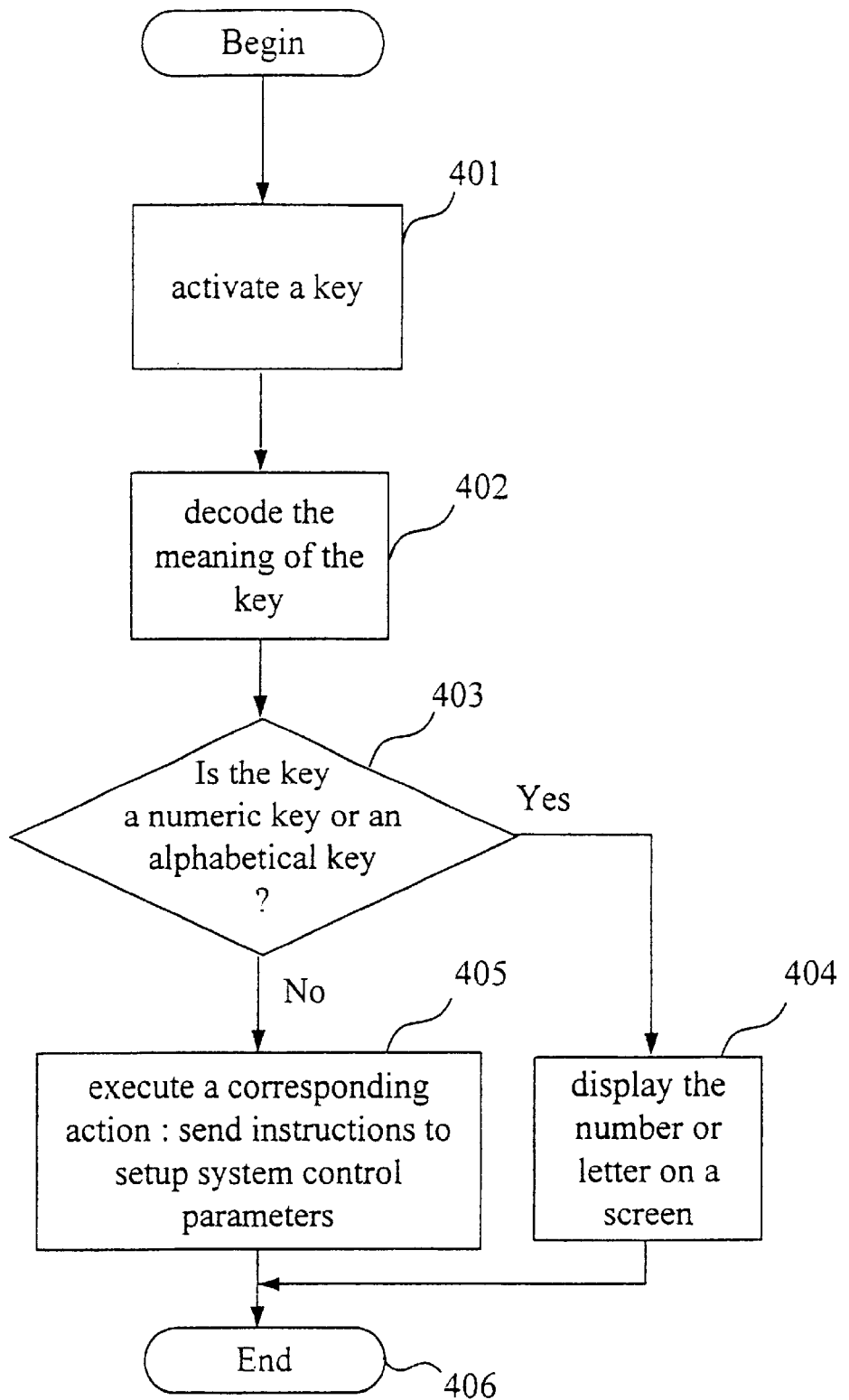
FIG. 4 shows a flow chart of the input data interpreting means of the present invention.

The circuit portion 104 includes a connector and circuit arrangement compatible with a keyboard, a mouse or a joystick of a personal computer. Therefore, the input devices of a personal computer can be used, instead of increasing an interface unit. To meet a need of the ultrasonic diagnostic system, an input data interpreting means 342 for interpreting the commands from users is placed beside the panel portion 101 of the personal computer. Steps executed by the input data interpreting means 342 are shown in FIG. 4. First, a key is entered or activated in step 401. In step 402, the meaning of the keys being pressed is decoded. In step 403, whether the received code is from numeric keys, alphabetical keys or function keys is determined. If the received code is from numeric keys or alphabetical keys, the entered number or letter is displayed on the screen 250 of the panel portion. If the received code is from function keys, then enter step 405, execute a corresponding action and send out instructions to setup system control parameters. After that, the computer goes to an end to wait for another entry.

The video capturing control unit 300 includes: a transducer connector 310 for receiving ultrasonic feedback signals from a scanning head 10; an ultrasonic preprocessor 320 for processing and determining the ultrasonic feedback signals and filtering possible noises; a system timing controller 330 for controlling the output of the ultrasonic preprocessor; and a host computer 340 for receiving instructions of the input data operation unit 100 which sets setting up parameters to control actions of the ultrasonic diagnostic system and message display of the video display unit 200. In the host computer 340, signals may be transmitted by a digital data output end to the video display unit 200.

The video display unit 200 includes: a digital scanning converter 210 for converting output video signals of the ultrasonic preprocessor 320 into digital video signals; a video display controller 230 for controlling the output of the digital video signals; and a digital display device 250 for selectively displaying one of the digital video signals of the video display controller 230 and digital data signals of the host computer 340. The digital display device 250 may be a device driven by digital control signals, such as a TFT-LCD display device. Therefore, the apparatus can be either used as a personal computer in a normal condition or used as an ultrasonic diagnostic system when connected to the scanning head 10.

The video display controller 230 includes: a video memory 233 for storing digital video signals; a video memory controller 231 for receiving and storing the digital video signals into the video memory 233; a synchronous signal generator 234 for generating at least one synchronous signal which is provided to the video memory controller 231 for outputting the digital video signals; and a video switch 240 for optionally outputting one of the digital video signals of the video memory controller 231 and digital data signals of the host computer 340 to the digital display device 250 such as a TFT-LCD. Besides, the video switch 240 can be controlled by software, and the digital video signals outputted by the video memory controller 231 will be sent to the TFT-LCD 250 through a digital video cable 232.

By the above structure, only an input data interpreting means is needed at input ends, such as a keyboard, instead of adding a special control interface. By the way, at output ends, there is no need to support a video capturing card, screen control card, and so on. In conclusion, the present invention supports an ultrasonic diagnostic system whose function is similar to a personal computer, and has a flexible utilization.

The above-described embodiments of the present invention are intended to be illustrated only. Numerous alternative embodiments may be devised by those skilled in the art without departing from the scope of the following claims.

What is claimed is:

1. An apparatus for human interfaces of an ultrasonic diagnostic system, comprising an input data operation unit, a video display unit and a video capturing control unit, wherein said video capturing control unit includes: a transducer connector for receiving ultrasonic feedback signals; an ultrasonic preprocessor for outputting video signals in response to said ultrasonic feedback signals; a system timing controller for controlling the output of the video signals from said ultrasonic preprocessor; and a host computer for receiving instructions from said input data operation unit and controlling system operations of said ultrasonic diagnostic system and message display of said video display unit;

said input data operation unit includes: a panel portion having a plurality of input devices for receiving commands from a user; and a circuit portion having a connector and circuit arrangement compatible with the input devices for transferring the commands to said host computer; and said video display unit includes: a digital scanning converter for converting the video signals of said ultrasonic preprocessor into digital video signals; a video display controller for controlling the output of said digital video signals; and a digital display device for selectively displaying one of the digital video signals of said video display controller and digital data signals of said host computer.

2. The apparatus for human interfaces of an ultrasonic diagnostic system of claim 1, wherein said host computer has an input data interpreting means for interpreting the commands transferred from said panel portion.

3. The apparatus for human interfaces of an ultrasonic diagnostic system of claim 1, wherein said video display controller has:

a video memory for storing the digital video signals;

a video memory controller for receiving and storing said digital video signals into said video memory;

a synchronous signal generator for generating at least one synchronous signal which is provided to said video memory controller for outputting said digital video signals; and a video switch for selectively outputting one of the digital video signals of said video memory controller and the digital data signals of said host computer to said digital display device.

4. An apparatus for human interfaces of an ultrasonic diagnostic system, said apparatus controlled by a host computer and outputting video signals from an ultrasonic preprocessor to function as an image output unit, comprising:

a digital scanning converter for converting the output video signals of said ultrasonic preprocessor into digital video signals;

a video display controller for controlling the output of said digital video signals; and a digital display device for selectively displaying one of the digital video signals of said video display controller and the digital data signals of said host computer.

5. The apparatus for human interfaces of an ultrasonic diagnostic system of claim 4, wherein said video display controller comprises:

- a video memory for storing digital video signals;
- a video memory controller for receiving and storing said digital video signals into said video memory;
- a synchronous signal generator for generating at least one synchronous signal which is provided to said video memory controller for outputting said digital video signals; and
- a video switch for selectively outputting one of the digital video signals of said video display controller and digital data signals of said host computer to said digital display device.

6. An apparatus for human interfaces of an ultrasonic diagnostic system, said apparatus controlled by a host computer and functions as an input data operation unit, comprising:

- a panel including numeric keys, alphabetical keys and function keys for inputting data and commands;
- a circuit portion for receiving said data and commands; and
- an input data interpreting means for interpreting the data and commands transferred from said circuit portion and then sending to said host computer.

* * * * *